(12) United States Patent
Ruzzier et al.

(10) Patent No.: US 9,097,868 B2
(45) Date of Patent: Aug. 4, 2015

(54) METHOD FOR CHECKING THE CORRECT INSTALLATION OF A BEND-INSENSITIVE OPTICAL CABLE AND OPTICAL CABLE SUITABLE FOR THE METHOD THEREOF

(75) Inventors: Marco Ruzzier, Milan (IT); Susanna Cattelan, Milan (IT); Andrea Macchetta, Milan (IT); Antonio Collaro, Milan (IT); Valeria Caronna, Milan (IT)

(73) Assignee: PRYSMIAN S.P.A, Milan (IT)

( * ) Notice: Subject to any disclaimer, the term of this patent is extended or adjusted under 35 U.S.C. 154(b) by 372 days.

(21) Appl. No.: 13/696,424

(22) PCT Filed: May 7, 2010

(86) PCT No.: PCT/IT2010/000206
§ 371 (c)(1),
(2), (4) Date: Feb. 12, 2013

(87) PCT Pub. No.: WO2011/138807
PCT Pub. Date: Nov. 10, 2011

(65) Prior Publication Data
US 2013/0142491 A1 Jun. 6, 2013

(51) Int. Cl.
*G02B 6/44* (2006.01)
*G01M 11/08* (2006.01)
(Continued)

(52) U.S. Cl.
CPC ........... *G02B 6/4401* (2013.01); *G01M 11/088* (2013.01); *G01M 11/3109* (2013.01); *G01N 21/84* (2013.01); *G02B 6/4463* (2013.01); *G02B 6/4413* (2013.01)

(58) Field of Classification Search
USPC ........................................................ 385/100
See application file for complete search history.

(56) References Cited

U.S. PATENT DOCUMENTS

| 5,130,535 | A | 7/1992 | Kummer et al. |
| 7,167,237 | B2 | 1/2007 | Shimizu et al. |
| 2006/0115224 | A1 | 6/2006 | Kutami et al. |

FOREIGN PATENT DOCUMENTS

| CN | 101576631 A | 11/2009 |
| EP | 1 256 826 A2 | 11/2002 |

(Continued)

OTHER PUBLICATIONS

Miles, "Locate fibre optic cable interrupting service", Fiber optic testing, Test, vol. 28, pp. 8-10, (Mar. 2002).

(Continued)

*Primary Examiner* — Sung Pak
(74) *Attorney, Agent, or Firm* — Finnegan, Henderson, Farabow, Garrett & Dunner, L.L.P.

(57) ABSTRACT

A method for detecting faulty laying down of an optical cable exhibiting a measured cut-off wavelength includes providing an optical cable for transmitting optical signals including at least one single-mode optical fiber having an attenuation equal to or larger than a first threshold value as measured when wound for one turn around a bending radius equal to or smaller than 5 mm at at least one predetermined test wavelength, the test wavelength being smaller than the measured cut-off wavelength, and an attenuation smaller than a second threshold value as measured when wound for one turn around a bending radius equal to at least a minimum bending radius at an operative wavelength equal to or larger than the measured cut-off wavelength; laying the optical cable; and measuring the attenuation in the at least one optical fiber at the predetermined test wavelength. An optical cable includes at least one optical fiber that is bend sensitive at a predetermined test wavelength not larger than the measured cut-off wavelength and is bend insensitive at an operative wavelength larger than the measured cut-off wavelength, where the cable operates in single-mode regime.

18 Claims, 5 Drawing Sheets

(51) Int. Cl.
*G01M 11/00* (2006.01)
*G01N 21/84* (2006.01)

(56) References Cited

FOREIGN PATENT DOCUMENTS

| EP | 2 116 877 A1 | 11/2009 |
|---|---|---|
| JP | 2-027231 | 1/1990 |
| JP | 4-351935 | 12/1992 |
| JP | 2004-198523 | 7/2004 |
| JP | 2009-204490 | 9/2009 |
| JP | 2009-204490 A | 9/2009 |
| WO | WO 2009/154712 A1 | 12/2009 |
| WO | WO 2010/051856 A1 | 5/2010 |

OTHER PUBLICATIONS

Unger et al, "Characterization of the bending sensitivity of fibers by the MAC-value", Optics Communications 107, pp. 361-364, (1994).
ITU-T Telecommunication Standardization Sector of ITU, "Series G: Transmission Systems and Media, Digital Systems and Networks, Transmission media characteristics—Optical fibre cables", G.652, pp. i-iv and 1-17, (Oct. 2000).
International Standard, "Optical fibres—Part 1-45: Measurement methods and test procedures—Mode field diameter" CEI IEC 60793-1-45, pp. 1-60, (Jul. 2001).
International Telecommunication Union, "ITU-T Telecommunication Standardization Sector of ITU , Series G: Transmission Systems and Media Digital Systems and Networks, Transmission media and optical systems characteristics—Optical fibre cables, Characteristics of a single-mode optical fibre cable", G.652, pp. 1-17, (Nov. 2009).
Clarke, et al., "Development and Application of a Long Wavelength OTDR to Provide Early Warning of Degradation in a Fibre Network", Proceedings of the 18th Australian Conference on Optical Fibre Technology, pp. 31-34, (1993).
Miles, "Locate fibre optic cable interrupting service", Fiber optic testing, Test, vol. 28, pp. 1 of 1, (Mar. 2002).
International Standard, "Optical fibres—Part 1-20: Measurement methods and test procedures—Fibre geometry", CEI IEC 6079 3-1-20, First Edition, pp. 1-53, (Sep. 2001).
ITU-T Telecommunication Standardization Sector of ITU, "Series G: Transmission Systems and Media Digital Systems and Networks Transmission media and optical systems characteristics—Optical fibres cables, Characteristics of a bending-loss insensitive single-mode optical fibre and cable for the access network", Recommendation ITU-T G.657, pp. i-iv and 1-13, (Nov. 2009).
International Standard, "Optical fibres—Part 1-44: Measurement methods and test procedures—Cut-off wavelength", CEI IEC 60793-1-44, First Edition, pp. 1-43, (Jul. 2001).
Unger, et al., "Characterization of the bending sensitivity of fibers by the MC-value", Optics Communications 107, p. 361, (1994).
International Search Report from the European Patent Office in International Application No. PCT/IT2010/000206 mailed Jan. 13, 2011.
Hatton, et al., "Accurately Predicting the Cutoff Wavelength of Cabled Single-Mode Fiber", Journal of Lightwave Technology, IEEE Service Center, New York, vol. 8, No. 10, XP000171577, pp. 1577-1583, (Oct. 1, 1990).
English-language translation of First Office Action issued Aug. 29, 2014 by the State Intellectual Property Office of the People's Republic of China in corresponding Application No. CN 201080057396.1 (11 pages).

METHOD FOR CHECKING THE CORRECT INSTALLATION OF A BEND-INSENSITIVE OPTICAL CABLE AND OPTICAL CABLE SUITABLE FOR THE METHOD THEREOF

CROSS REFERENCE TO RELATED APPLICATION

This application is a national phase application based on PCT/IT2010/000206, filed May, 7, 2010, the content of which is incorporated herein by reference.

TECHNICAL FIELD

The present invention relates to a method for checking the installation and/or the laying of a bend-insensitive optical cable and to an optical cable that is bend-insensitive when operating in single-mode regime.

BACKGROUND OF THE INVENTION

The use of single-mode optical fibres in fibre-to-the-premises (FTTP) applications, including fibre-to-the-home (FTTH) and fibre-to-the-building (FTTB) applications, generally require low bending loss of optical signals transmitted through the fibres, also under stringent installation constraints that may impose tight bend radii, e.g., due to sharp cornering in buildings or compression of optical fibres. In particular, cabling and hardware applications aimed to miniaturize passive field equipment, e.g., local convergence cabinets or storage boxes, and the development of multi-dwelling units (MDUs) require fibre designs with superior bending capabilities. In addition, coarse wavelength division multiplexing systems (CWDM) and passive optical network (PON) systems may also need employment of bend-insensitive optical fibres.

In order to standardize the bending performance of optical fibres particularly suited for FTTP applications, the ITU-T (International. Telecommunications Union, ITU Telecommunication Sector) has recently developed recommendation G.657 (11/2009) that defines single-mode fibres with enhanced bending performance.

To conform to international standards, besides bending capabilities, fibre performance can be evaluated also on other relevant optical parameters such as the cut-off wavelength and the mode field diameter (MFD). A parameter that can be useful for finding a compromise among the MFD, the cut-off wavelength and bending losses is the so-called MAC number, which is the ratio of the MFD and the cut-off wavelength.

It has been observed that in order to obtain low bending losses, the MAC number should be reduced. In *Characterization of the bending sensitivity of fibres by the MAC value*, by C. Unger and W. Stocklein, published in Optics Communications, vol. 107 (1994), pages 361-364, macro- and microbending performance of matched-cladding fibres and correlation with the MAC number are investigated. The articles states that the bending behaviour of step-index fibres is completely characterized by the MAC number and that macro- and micro-bending losses increase with increasing of MAC number.

Patent application WO 2009/154712 describes an optical fibre cable comprising two optical fibres, each fibre being a microstructured bend performance fibre. Optical fibre cables of the disclosed solution are said to allow aggressive bending such as for installation, slack storage, and the like while inhibiting bend radii that allow damage and/or breaks of the optical fibre.

During installation and deployment of optical cables, in-field testing of optical attenuation is generally performed in order to detect faults in fibre networks. Such optical tests are performed by means of transmission and/or reflection measurements, and typically by optical time-domain reflectometry (OTDR) techniques.

U.S. Pat. No. 7,167,237 discloses a fault searching system for an optical line from a user optical terminal to an optical divider, without affecting other user optical terminals and transmission apparatuses, from the user optical terminal side by connecting an OTDR being to a terminal portion of the optical line in the user optical terminal, and by using at least one of those in which a value of a wavelength used in the OTDR connected is set to a value different from a value of a wavelength used for data transmission in the optical line, and a peak level of an optical pulse is set to a predetermined level or less. The wavelength of the test light is a wavelength different from the wavelength of the light used for data transmission in the optical line, in particular a value included in one of ranges being greater than or equal to 0.3 µm and less than 1.3 µm or greater than 1.65 µm and less than or equal to 2.0 µm.

K. Clarke and A. Duncan in *"Development and Application of a Long wavelength OTDR to provide Early warning of Degradation in a Fibre Network"*, published in the Proceedings of the 18th Australian Conference on Optical Fibre Technology, 28 Nov.-1 Dec. 1993, pp. 31-34, describes an OTDR operating at 1662 nm for out-of-band monitoring to overcome the disadvantages of monitoring at wavelengths that are the same as those used to carry traffic on the fibre.

D. Miles in *"Locate fiber optic cable interrupting service"*, published in Test, vol. 28, no. 2 (March 2002), pp. 8-10, describes tests with a multiple-wavelength OTDRs that test out-of-band wavelengths. Higher wavelengths, i.e. 1625 nm, are said to be highly effective for spotting bends that can later develop into breaks or stress- or temperature-losses.

Patent Abstracts of Japan of JP 4-351935 describes a light pulse testers which use longer and shorter testing wavelength than the signal wavelength and a light band path filter. The abstract reports that the backscattering obtained with the longer wavelength testing light is to sensitively test and monitor the bending loss of the optical fibre, whereas the backscattering obtained with the shorter wavelength testing light is to sensitively test and monitor the connection loss of the fibre.

Patent application JP 2-027231 relates to an optical fibre lengthwise distortion measurement method using a first-wavelength light formed from the wavelength used in optical signal transmission in the optical fibre being measured as well as a second-wavelength light formed from at least one of the wavelengths with a bigger occurrence of optical loss for the respective types of distortion amounts in the optical fibre being measured than the wavelength of the first-wavelength light, the entry of each optical pulse of the first-wavelength light and second-wavelength light from one end of the optical fibre being measured, and the measurement of distortion such as bending of the optical fibre being measured based on comparative evaluation of the difference of the attenuation amount of each optical pulse of the first-wavelength light and second-wavelength light reflected in the optical fibre being measured as well as the difference of the variation over time of the attenuation amount.

OTDR tests can provide useful information about the possible presence of tight bends, in particular bends of a radius smaller than the minimum radius recommended by the manufacturer, which might adversely affect the mechanical lifetime of the fibre.

Tight bends may be introduced accidentally during laying down or be the result of less careful deployment practices that may be used to speed up the installation process, such as aggressive stapling of optical drop cables and sharp-angle deployment around corners. In particular, a tight bending radius may cause cracks on the surface of the optical fibre, which gradually extend and may eventually lead to a permanent damage or rupture of the fibre. Long-time mechanical reliability of the fibre can depend on the capability of detecting the presence of dangerous bends.

Patent application US 2006/0115224 describes a single-mode optical fibre having a cut-off wavelength in a 1.31 μm wavelength band, in which a relative refractive index difference of the core with respect to the cladding is adjusted such that a bending loss, when a bend is applied in a radius smaller than a limit bending radius, becomes greater than a detection limit value, the limit bending radius being calculated from a relationship between a bending radius applied to the optical fibre and a failure probability occurs after a predetermined time period. In an embodiment, the fibre has a step-index profile. Disclosed results from a step-index optical fibre indicate that, when the refractive index difference between the core and the cladding is greater than about 0.80%, the loss caused by a bend is reduced to about 0.01 dB/turn or less in a limit bending radius of 5.5 mm, which it is said to make measurements using an OTDR difficult. Optical measurements on the fibre are performed at transmission wavelengths of 1.31, 1.55 and 1.625 μm.

Patent application EP 1 256 826 A2 discloses an optical fibre design constructed to prevent theft of optical signals. One technique to allow tapping of a portion of the signal theft of optical signals is to form a bend in the fibre that causes "leaking" of the optical signal into the fibre cladding where it can be intercepted without the source or the receiving station. This case of intrusion is addressed by increasing the sensitivity of the optical fibre to microbending loss to the extent that bends in the fibre causes such a high attenuation that bends do not go undetected. A high bend sensitive fibre is produced by introducing an undoped outer ring region at a substantial distance from the fibre core. The document mentions that such bend sensitive designs do not adversely impact transmission properties, provided that the fibre cable, is installed to have a large minimum bending radius.

Patent application PCT/EP2008/065174 filed by the instant Applicant on Nov. 7, 2008 relates to an optical cable having a cable length extending from an input end to an output end and comprising at least one single-mode optical fiber having a cable cut-off wavelength of from 1290 nm to 1650 nm, wherein said at least one optical fiber is helically twisted around a longitudinal direction for a twisted length L with a twisting pitch P, the values of L and P being selected such that the optical cable exhibit substantial single-mode transmission, and wherein said twisted length L extends along at least a portion of said cable length. In particular, the twisted length L and the twisted pitch P are selected in such a way that the measured cut-off wavelength in the optical cable is equal to or lower than 1260 nm.

SUMMARY OF THE INVENTION

In compliance with the always more stringent requirements of bend insensitiveness for optical fibres, recent developments for FTTP applications are directed to highly bend-insensitive optical fibres. The Applicant has observed that, if the fibre is highly bend-insensitive, even a mechanically dangerous bend would not generate a measurable optical attenuation within the wavelength range of signal transmission, at least when using standard equipment for in-field testing. Therefore, if on one hand bend-insensitivity is required to guarantee cost-effective installation and optical performance, on the other hand, it may preclude early in-field detection of harmful bends, thereby increasing the risk of higher repair and maintenance costs.

The Applicant has realised that if an optical cable is designed so as to exhibit bend insensitivity in a wavelength region of single-mode operation of the optical cable (i.e., the wavelength region comprising an operative wavelengths, but bend sensitivity at at least one wavelength outside said wavelength region, it is possible to detect dangerous bends without affecting the bend performance of the cable.

An aspect of the present invention is a method for detecting faulty laying down of an optical cable exhibiting a measured cut-off wavelength, measured after propagation over a cable length, the method comprising:

providing an optical cable for transmitting optical signals including at least one single-mode optical fibre having an attenuation equal to or larger than a first threshold value as measured when wound for one turn around a bending radius equal to or smaller than 5 mm at at least one predetermined test wavelength, the test wavelength being smaller than the measured cut-off wavelength, and an attenuation smaller than a second threshold value as measured when wound for one turn around a bending radius equal to at least a minimum bending radius at an operative wavelength equal to or larger than the measured cut-off wavelength;

laying the optical cable, and measuring the attenuation in the at least one optical fibre at the predetermined test wavelength.

Another aspect of the invention is an optical cable that exhibits single-mode transmission and is bend-insensitive at wavelengths equal to or higher than a measured cut-off wavelength after propagation over a cable length. Preferably, the measured cut-off wavelength is equal to or smaller than 1260 nm. The optical cable comprises at least one optical fibre that is bend sensitive at a predetermined test wavelength not larger than the measured cut-off wavelength and is bend insensitive at an operative wavelength equal to or larger than the measured cut-off wavelength, where the cable operates in single-mode regime.

In some preferred embodiments, the wavelength region of single-mode operation corresponds to the transmission wavelength band, which is, in most cases of interest, of from 1260 nm to 1675 nm, although recently introduced international standards in single-mode optical transmission tend to stretch out the transmission band, for example towards a larger upper limit.

Within the present context, with "bend sensitive/sensitivity" it is meant that attenuation, i.e. transmission loss, as measured in an optical fibre in cabled or uncabled configuration when wound for one turn around a bending radius equal to or smaller than 5 mm, is equal to or larger than a first threshold value, hereafter referred also as the detection threshold value.

Preferably, the detection threshold value is set to be equal to or larger than a detection limit of the test optical system for checking the attenuation in the optical cable. In some embodiments, the detection limit is equal to or higher than about 0.1 dB so that cost-efficient technical equipment can be used to check the optical cables. However, use of higher- or lower-sensitivity systems is not excluded from the present disclosure and therefore the detection threshold value can be set at a different, e.g. smaller or larger value of bending loss, depending on the specific cable type and use and the detection apparatus which is used.

With "bend insensitive/insensitivity" it is meant that attenuation as measured in an optical optical fibre in cabled or uncabled configuration when wound for one turn around a bending radius equal to at least a minimum bending radius is lower than a second threshold value. Preferably, the minimum bending radius is of 7.5 mm, more preferably of 5 mm. For example, the second threshold value is a predetermined value set by international standards, such as recommendation ITU-T G.657 (11/2009). In an embodiment, the second threshold value is of 0.1 dB. In an embodiment, the first threshold value is larger than the second threshold value. In another embodiment, the first and second threshold values are approximately equal.

Preferably, the optical cable exhibits bend sensitivity at at least one test wavelength smaller than 1260 nm, more preferably of equal to or larger than 450 nm and smaller than 1260 nm, still more preferably of from 600 nm to 1200 nm. In a preferred embodiment, the test wavelength is of from 800 to 1000 nm. For example, the test wavelength is of 850 nm, which corresponds to an operating wavelength of commercially available OTDR equipments for testing of multi-mode optical fibres, typically having as light source a VCSEL source.

In accordance with some preferred embodiments of the present invention, bend resistance of the optical cable is provided by selecting at least one fibre having per se an optical parameter non compliant with the common standards, namely a relatively large cable cut-off wavelength for reduction of the fibre MAC number, and arranging the fibre within the cable by imparting a curvature to at least one longitudinal portion of said fibre. In particular, by twisting the at least one fibre around a longitudinal axis with a twisting pitch and for a twisted length, the effective fibre cut-off wavelength decreases and thus the resulting cut-off wavelength measured in the optical cable can be lowered to a value satisfying the desired optical performances for single-mode transmission. In many cases of interest, the optical cable exhibits single-mode transmission at wavelengths equal to or higher than 1260 nm.

Preferably, the cable cut-off wavelength, $(\lambda_{cc})_A$, of the at least one optical fibre is equal to or larger than 1290 nm, more preferably of from 1290 nm to 2200 nm, even more preferably of from 1600 nm to 2000 nm.

In some embodiments, the twisting pitch P is selected in the range from 5 mm to 30 mm, preferably from 5 to 20 mm.

Preferably, the twisted length L of the optical cable is selected by taking into account the value of the twisting pitch P.

In some embodiments, the twisted length L is of at least 2 meters. In some embodiments, the twisted length is equal to or smaller than 2 km.

Preferably, the twisted length L is approximately equal to the cable length.

Preferably, the at least one optical fibre have a match-clad refractive index profile, more preferably a step-index profile. Step-index fibres often entail a low complexity of the preform manufacturing at the benefit of the cost of the finished product.

Preferably, the at least one optical fibre has a step-index profile having a maximum relative refractive index of from 0.5% to 1% and an outer core radius of from 4 μm to 7 μm.

In some embodiments, the at least one optical fibre comprised in the optical cable is selected to have an MFD of at least 8.6 μm, for example up to 9.5 μm, preferably of from 8.6 μm to 9.0 μm. A value of MFD compliant to the ITU-T standards, can allow ease of operation and relatively small insertion loss, e.g., less than 0.1 dB, in fusion and/or mechanical splicing of the optical cable.

According to a preferred embodiment, the optical cable comprises two optical fibres twisted together along the longitudinal direction for a given twisted length.

According to another preferred embodiment, the optical cable comprises an optical fibre twisted around a central element extending along the longitudinal direction.

In some embodiments, the optical cable comprises at least one single-mode optical fibre that is bend sensitive at at least one predetermined test wavelength for testing use; and at least one bend insensitive single-mode optical fibre dedicated to the transmission.

In some embodiments, the optical cable according to the invention can be used as drop cable in a fibre access distribution network.

BRIEF DESCRIPTION OF THE DRAWINGS

The present invention will be now described more fully hereinafter with reference to the accompanying drawings, in which some, but not all embodiments of the invention are shown.

DEFINITIONS

Figure 1:
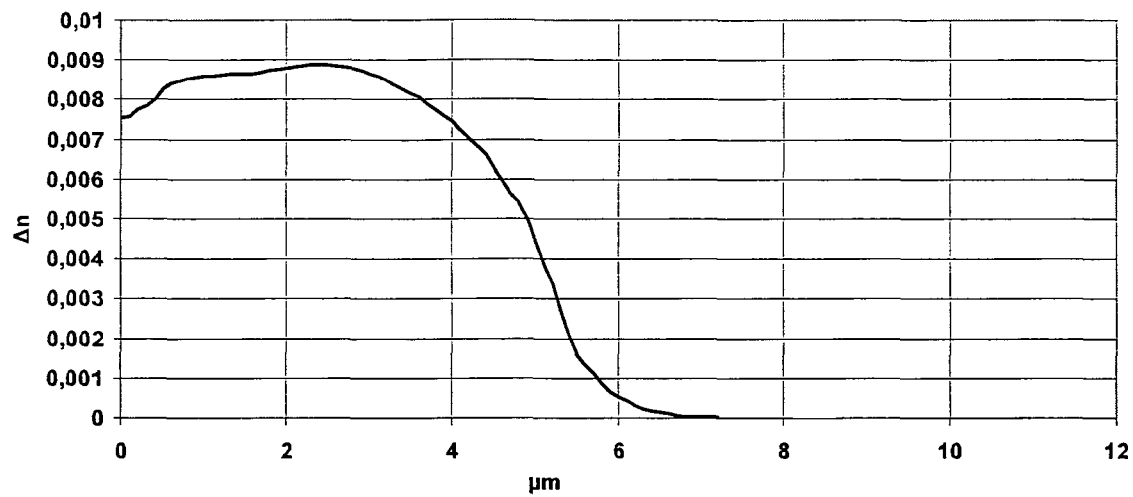
FIG. 1 is a graph showing an exemplary refractive index profile of an optical fibre comprised in an optical cable according to some embodiments of the invention.

Measured cut-off wavelength is defined according to IEC-60793-1-44 (2001-07) standard as the wavelength greater than the one at which the ratio between the total power, including launched higher-order modes, and the fundamental mode power has decreased to less than 0.1 dB. According to this definition, the second-order mode ($LP_{11}$) undergoes 19.3 dB more attenuation than the fundamental mode ($LP_{01}$). Herein, given an optical cable of cable length $L_{TOT}$, the measured cut-off wavelength is generally referred to the cut-off wavelength measured according to the IEC-60793-1-44 standard definition in the cable length, $L_{TOT}$, when the cable is substantially linearly deployed.

Cable cut-off wavelength of an optical fibre $(\lambda_{cc})_A$ is the cut-off wavelength value measured according to the cut-off test Method A described in the IEC-60793-1-44 (2001-07) standard. Namely, the method A prescribes to perform the measurement on a 22 m of uncabled fibre span, where the central 20 m portion of the fibre is wound on a 280 mm-diameter mandrel and one turn of each of the two 1 m-long end portions is wound on a 80 mm-diameter mandrel.

Cable cut-off wavelength of an optical cable $(\lambda_{cc})_B$ is the cut-off wavelength value measured according to the cut-off test Method B described in the IEC-60793-1-44 (2001-07) standard. The measurement is performed on a 22 m-long optical cable, where the central 20 m portion of the cable is linearly deployed and the fibre is for two 1 m-long end portions, which are wound on a 80 mm-diameter mandrel.

The mode field diameter (MFD) of an optical fibre is measured according, to the IEC 60793-1-45 (2001-07) standard, at a wavelength of 1310 nm.

MAC number is defined as the ratio between mode field diameter (MFD) measured at 1310 nm, in microns, and the cable cut-off wavelength $(\lambda_{cc})_A$, in microns.

Match-clad optical fibres are fibres whose refractive index profile has substantially no regions with index significantly lower than that of the outer cladding taken as a base reference (in most cases, pure silica), at the wavelengths used in single-mode transmission. Typically, a match-clad optical fibre is substantially free from index-decreasing dopants in the core.

In the present description and claims, the term "drop cable" is used to refer to an optical cable operating as the last link of an access distribution network, typically, but not exclusively, serving just one subscriber.

DETAILED DESCRIPTION

Bend-insensitive optical cables comprising single-mode optical fibres are often tailored to FTTP applications, where they are provided in houses, offices, and other premises for telecommunication services, such as broadband Internet, video-on-demand and high-definition IPTV. An access distribution can be deployed on a single floor of a building or generally installed in a multi-story building in order to bring optical fibres to individual subscribers on different floors. For example, in a multi-store building, a distribution network may comprise a MDU placed on the building's basement from which a riser cable traverse the vertical rise of the building and segments of the cable are dropped at each floor. Alternatively, the distribution cable can be routed from an optical network unit and is spliced up at a plenum cable entrance facility in a plurality of drop cables that then reach different houses of individual subscribers.

Installation routes of drop cables often include tight corners and edges, such as in case when the cable runs around a doorframe or around a sharp corner within an apartment.

As is well known, propagation modes of the optical signals are attenuated by fibre bends. Generally speaking, bend-induced attenuation, herein referred also to as bending loss, increases with increasing wavelength and with decreasing bending radius. For a given bending configuration, the cut-off wavelength of a single-mode fibre is the wavelength above which the fibre propagates only the fundamental mode. Below cut-off, the fibre will transmit more than one mode. The cut-off wavelength in general depends on the refractive index profile of the optical fibre and on the bending configuration, such as in-field deployment and cable construction.

Demand of optical fibres and cables with enhanced performance under severe bending is increasing, also to conform to the recently developed recommendations ITU-T G.657 (11/2009). Although a typical FTTP deployment can be expected not to induce a bend with radius of less than 7.5 mm, preferably of equal to or smaller than 5 mm, tighter bends may be accidentally be introduced and/or be the result of less careful, less expensive deployment practices. Tighter bends can put at risk the mechanical reliability of the optical fibres and thus of the cable. In bend-insensitive optical fibres designed to conform to the more stringent optical bend performance, the occurrence of a mechanically dangerous bend originated by the laying down of the cable containing the fibres may not generate an optical attenuation measurable by the optical test equipments typically employed in in-field testing.

The Applicant has understood that if the optical cable (fibre) is required to be bend insensitive in a wavelength transmission band, bend sensing should be performed in a wavelength region outside the transmission wavelength band. The Applicant has realised that if an optical cable is designed so as to exhibit bend sensitivity outside the wavelength region comprising an operative wavelength in which the cable operates in single-mode, but bend insensitivity within said region, it is possible to detect potentially dangerous bends without affecting the bend performance of the cable.

To conform to international standards, besides bending capabilities, fibre performance is evaluated also on other relevant optical parameters such as the cut-off wavelength and the mode field diameter (MFD). Macrobending losses have a general tendency to decrease with decreasing of the MAC number of the optical fibre. The MAC number of an optical fibre is defined by the following relation:

$$MAC = \frac{MFD}{(\lambda_{cc})_A} \tag{1}$$

where MFD is the mode field diameter at 1310 nm, measured in microns, and $(\lambda_{cc})_A$ is the cable cut-off wavelength of the fibre, always in micron. In general, macrobending loss decreases with decreasing the MAC number. A low MAC value can be achieved either by lowering the MFD or by increasing the $(\lambda_{cc})_A$, or by acting on both optical parameters. However, to conform to international standards, besides bending capabilities, the optical fibre is often required to possess several relevant optical parameters, in particular the cable cut-off wavelength and the MFD, within a prescribed range of values. For example, ITU-T Recommendation G. 652 (10/2000, optical fibres for standard transmission) recommends an MFD at 1310 nm of at least 8.6±0.4 μm and the cable cut-off wavelength of the optical fibre, always according to G. 652, should be not larger than 1260 nm, i.e., well below a typical operative wavelength of 1310 nm.

The Applicant has understood that by selecting an optical fibre with cable cut-off wavelength above the values that permit single mode transmission in accordance to the requirements prescribed by common transmission standards it is possible to obtain an optical cable with single-mode optical performance by imparting a curvature with a radius of curvature to at least a length portion of the optical fibre comprised in the cable.

FIG. 1 is a graph illustrating the relative refractive index profile, Δn, of an exemplary single-mode optical fibre comprised in an optical cable according to an embodiment of the present invention, as a function of the radial distance $r_C$ from the centre of the fibre ($r_C$=0, i.e. the y-axis of the graph represents the centreline of the optical fibre). The fibre comprises a core region surrounded by a clad region and has a step-index profile with positive relative refractive index Δn in the core region with respect to the clad region. The fibre core is preferably made of silica doped with a doping element that increases the refractive index, such as germanium. Given that the clad region of single-mode optical fibres used for transmission is generally made of pure (undoped) silica, the relative index profile takes as a reference the refractive index of the clad region. In the embodiment of FIG. 1, the cladding region is of pure silica, Δn=0.

In the following, reference will be made to the relative refractive index percent, Δ%=Δn×100. For a step-index fibre, the two main parameters that can characterise a step-index optical fibre are the maximum relative refractive index percent, $\Delta_{max}$%, and the outer core radius, $r_C$, the latter being defined according to IEC 60793-1-20 (2001-09), Annex C. The maximum relative refractive index and the outer core radius are selected to provide a transmission loss of equal to or larger than a first threshold value (i.e. the detection threshold value) for wavelengths smaller than 1260 nm and transmission loss smaller than a second threshold value for wavelengths equal to or larger than 1260 nm. More generally, the maximum relative refractive index and the outer core radius are selected to provide a transmission loss of equal to or larger than a first threshold value for wavelengths smaller than a cut-off wavelength measured in an optical cable comprising the optical fibre and smaller than a second threshold value for wavelengths equal to or larger than the measured cut-off wavelength of the cable.

In the preferred embodiments, the outer core radius is of from 4 μm to 7 μm and the maximum relative refractive index percent is of from 0.5% to 1%. Preferably, the maximum relative refractive index percent is of from 0.7% to 1%. Preferably, the outer core radius is of from 5 μm to 7 μm.

Preferably, the cable cut-off wavelengths, $(\lambda_{cc})_A$, of the optical fibre is not smaller than 1290 nm, more preferably not smaller than 1600 nm. In some preferred embodiments, the cut-off wavelengths is of from 1290 nm to 2200 nm, more preferably of from 1600 nm to 2000 nm. A relatively high value of cable cut-off wavelength leads to a relatively small MAC number and thus improves the resistance of the fibre to macrobending. With reference to common ITU-T recommendations for optical signal transmission, the optical fibre is thus single-mode at cable cut-off wavelengths, $(\lambda_{cc})_A$, larger than the values recommended.

In the example shown in FIG. 1, $\Delta_{max}$%=0.89% and $r_C$=5.8 μm The value of said parameters were selected to obtain a cable cut-off wavelength $(\lambda_{cc})_A$ of about 1750 nm. The MFD value at 1310 nm is of 8.4 μm. This optical fibre exhibits transmission loss of less than 0.1 dB measured for a winding of one turn around a bending radius of 5 mm at wavelengths within the transmission band of from 1260 nm to 1650 nm and transmission loss of not less than 0.1 dB for wavelengths within the range 650 nm to 950 nm. It is noted that for the optical fibre of this example the first threshold value is equal to the second threshold value. It is to be understood that the first and second threshold values can be different, for example the second threshold value can be smaller than the first threshold value, e.g. 0.05 dB.

By selecting suitable values of $r_C$ and $\Delta_{max}$% within the above described ranges it is possible to select the bending sensitivity of the optical fibre at a predetermined test wavelength.

The optical fibre described above can be obtained by standard manufacturing processes, such as an outside vapour deposition (OVD) process.

According to a particular aspect of the preferred embodiments of the present invention, a twist is imparted to the at least one optical fibre comprised in the optical cable for at least a length portion of the cable length in such a way that the cable cut-off wavelength of the fibre decreases and thus the resulting cut-off wavelength measured in the optical cable over the cable length satisfies the desired optical performances for single-mode transmission at wavelengths not smaller than a desired effective cut-off wavelength, e.g. equal to or smaller than 1260 nm.

Figure 2:
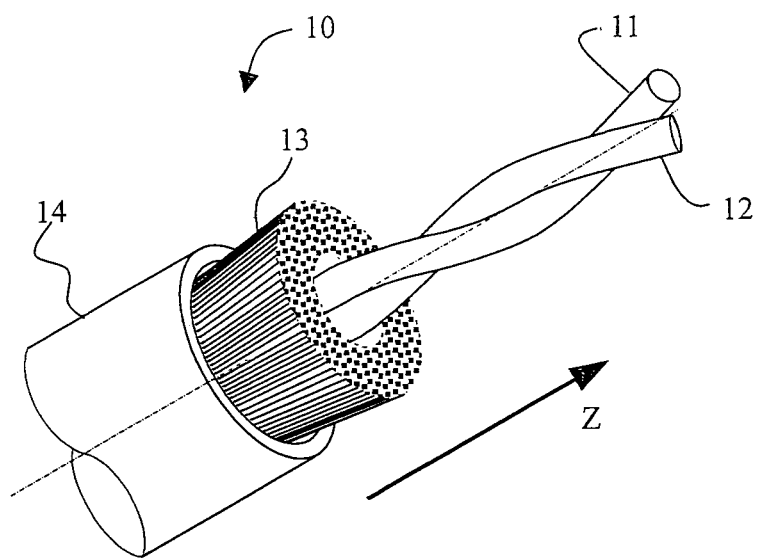
FIG. 2 is a schematic perspective view of an optical cable according to an embodiment of the present invention.

FIG. 2 is a schematic perspective view of an optical cable according to an embodiment of the present invention. The optical cable 10, which can be a drop cable of an access distribution network, comprises two optical fibres 11 and 12 helically twisted around each other along a longitudinal axis Z (i.e., the helical axis), which is in general substantially parallel to the cable longitudinal direction. The optical cable 10 extends for a total length, $L_{TOT}$, from an input end adapted to receive the optical signals to be transmitted to an output end. The input and output ends are not shown in the figure, which represents only a portion of the cable in order to illustrate the cable construction. The optical fibres 11 and 12 are twisted for a twisted length, L, with a twisting pitch P, which corresponds to a radius of curvature, ρ. The cable has a measured cut-off wavelength measured after propagation of the light over the total length, $L_{TOT}$.

Each fibre 11 and 12 is single-mode and has an attenuation equal to or larger than a first threshold value as measured for a winding of one turn around a bending radius not larger than 5 mm at a predetermined test wavelength smaller than the measured cut-off wavelength and an attenuation smaller than a second threshold value as measured for a winding of one turn around a bending radius equal to at least a minimum bending radius, which is preferably of 7.5 mm, more preferably of 5 mm, at an operative wavelength equal to or larger than the measured cut-off wavelength of the cable.

In some embodiments, fibres 11 and 12 are made of silica-based materials and comprise a core surrounded by a cladding. Preferably, the optical fibres of cable 10 have a step-index profile with the outer core radius of from 4 μm to 7 μm and the maximum relative refractive index percent is of from 0.5% to 1%. Preferably, each optical fibre has a cable cut-off wavelength of from 1290 to 2200 nm, more preferably of from 1600 nm to 2000 nm.

According to an embodiment, the fibres 11 and 12 of optical cable 10 are "tight-buffered". The silica optical fibre, with typical nominal diameter of 125 μm, is coated by a primary coating, which is surrounded by a secondary coating, which typically contacts the primary coating, the primary and secondary coating forming a coating system. For example, the coating system is made of two different UV-cured acrylate material up to a diameter of 250 μm. A buffer layer is provided to surround the coating system in a tight manner, i.e., substantially homogeneously adhering to the fibre coating system. Advantageously, the buffer layer is made of a thermoplastic material, preferably an LSOH (Low-Smoke Zero Halogen) material. The buffer layer is typically extruded over the 250 μm-coated fibre, increasing the outside diameter up to 600-1000 μm, with typical values of 800-900 μm.

According to another embodiment, the optical fibres of the optical cable are coated only by a coating system and have an outside diameter of about 250 μm.

The optical cable of FIG. 2 illustrates a loose-tube buffer construction, in which the twisted fibres are inserted in a longitudinally extending tubular jacket 14, made of a polymeric material, for instance of a thermoplastic material. Within the jacket 14, the twisted fibres are surrounded by strengthening members 13, such as aramid yarns. For example, the fibres have an outside diameter of 900 μm and the jacket 14 has an inner diameter of 2-3 mm and an outer diameter of 4-5 mm.

One way of producing the optical cable represented in FIG. 2 is by selecting a given span length of two tight-buffered optical fibres. The span length of each fibre can be for instance of 15-20 m, which can be typical for producing a cable for indoor FTTP applications, such as a drop cable. For example, a cable comprising two optical fibres according to the invention was produced as follows. Two buffered optical fibres are loaded on a pair-twisting and stranding module, commonly used for the production of copper stranded pair cables. Said module comprised a double pay-off, a bow for twisted pair formation, and a rotating drum take-up. The combined twisting of pay-off and take-up determines the twisting pitch.

Figure 3:
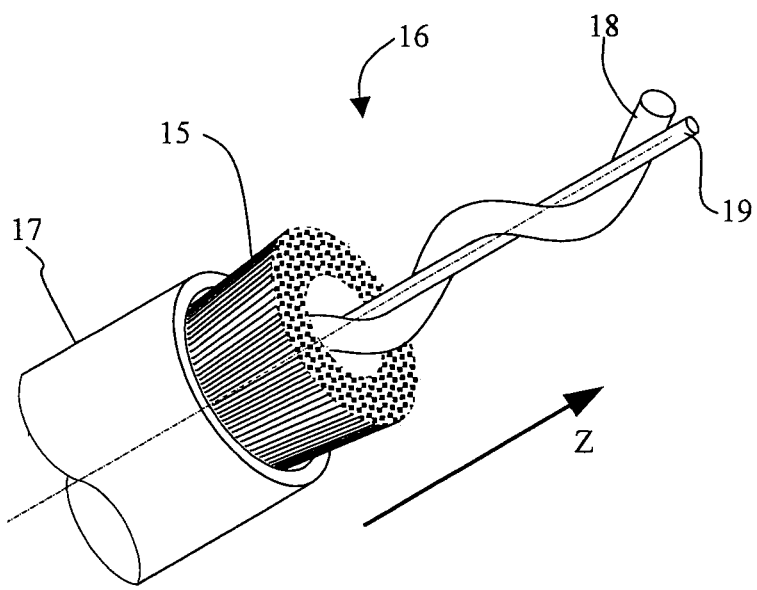
FIG. 3 is a schematic perspective view of an optical cable according to another embodiment of the present invention.

According to an embodiment of the present invention, the bend-insensitive optical cable comprises one optical fibre only. FIG. 3 is a schematic representation of an optical cable 16 comprising an optical fibre 18, which is helically wound around a central element 19 that extends along a longitudinal direction Z, substantially corresponding to the axis about which the optical fibre is wound, i.e., the helical axis. The cable 16 has a measured cut-off wavelength measured after propagation of the light over the total length. The optical fibre 18 is a single-mode optical fibre having an attenuation not smaller than a first threshold value as measured for a winding of one turn around a bending radius not larger than 5 mm at a predetermined test wavelength smaller than the measured cut-off wavelength and an attenuation below a second threshold value as measured for a winding of one turn around a minimum bending radius of 7.5 mm, preferably of 5 mm, at an operating wavelength equal to or larger than the measured cut-off wavelength of the cable. The optical fibre 18 (when in an untwisted state) has a cable cut-off wavelength larger than 1290 nm, preferably of from 1600 to 2000 nm.

In an embodiment, the optical fibre 18 is "tight buffered", namely it comprises an optical fibre, made e.g., of silica glass, surrounded by a coating system, which is in turn surrounded by a buffer layer. The outside diameter of the optical fibre can range for example from 600 to 1000 μm. The central element 19 can be for instance a rod of GRP (Glass Reinforced Polymer) of outer diameter of 1 μm.

The optical cable 16 including the twisted optical fibre 18 has a loose-tube buffer construction comprising strengthening members, such as water-absorbing filaments, 15 applied over the twisted optical fibre and a tubular jacket 17. It is to be understood that the presence of strengthening members 15 in the optical cable is optional.

The embodiment of FIG. 3 can be advantageous if a reduced cross-sectional dimension of the cable is required, e.g., of less than a few mm of diameter. In such a case, the central element 19 can be of a relatively small diameter, e.g., of 0.5 mm.

Preferably, the at least one optical fibre comprised in the optical cable according to the invention has a MFD value sufficiently large to support ease of operation and limited insertion loss in fusion and mechanical splicing. Preferably, the MFD value is of from 8.6 to 9.5 μm.

Figure 4:
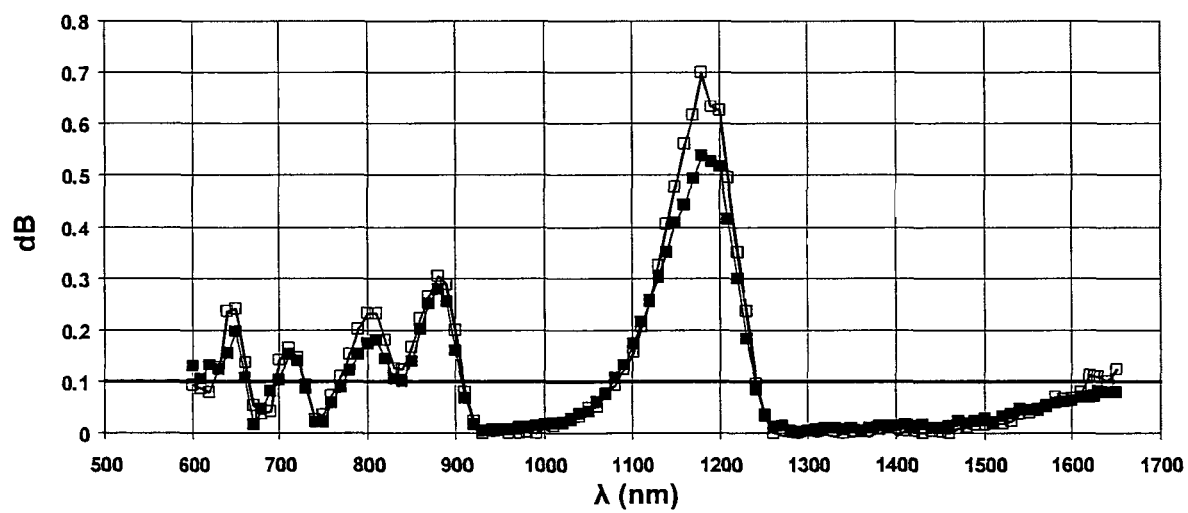
FIG. 4 is a graph showing experimental measurements of macrobending loss of an optical cable according to an embodiment of the present invention, measured in the wavelength band from 600 nm to 1650 nm for straight cable deployment and for 10 loops with 10 mm bending radius on bare fibre at both cable ends.

FIG. 4 is a graph showing experimental measurements of attenuation of a 20 m long section of an optical cable ($L_{TOT}$=20 m) according to an embodiment of the present invention, measured in the wavelength band from about 600 nm to 1650 nm. The cable has a configuration of the type shown in FIG. 2 and twisted length approximately equal to the cable length. In particular two single-mode optical fibres having a step-index profile are twisted together with a twisting pitch of 9.9 mm. Each fibre is buffered and has an outside diameter of 900 μm. The cable is wound for one turn around a mandrel of 3 mm of radius. Filled squares represent measurements for the cable with straight cable deployment (but for the winding of 3 mm radius at a cable middle portion), whereas empty squares represent measurements in a cable where 10 loops of 10 mm bending radius—in addition to the one-turn winding of 3 mm radius at a cable middle portion— were applied to the cable to simulate a deployment path with angles and corners. A thick solid line draws the selected threshold value for bend sensitivity, which is set to correspond to a detection threshold of 0.1 dB of an exemplary optical test system. The measured cut-off wavelength after propagation over the 20 m length is of about 1250 nm.

For both cable deployments, results of FIG. 4 show that for wavelengths larger the cut-off wavelength of the cable (at about 1250 nm) and up to about 1650 nm attenuation remains smaller than 0.1 dB. At wavelengths smaller than 1260 nm, a plurality of attenuation peaks exceeding the detection threshold is visible. In particular, there exist pronounced peaks at about 640 nm, 800 nm, 890 nm and at 1150 nm. From the comparison between the two experimental curves of FIG. 4, spectral attenuation does not appear to be significantly affected by the presence of the 10 mm bending radius loops.

A fibre cable as that of the results shown in FIG. 4 can be probed at a test wavelength corresponding to one of the attenuation peaks in the wavelength window below the cut-off wavelength of the cable measured across the cable length. Therefore, in the transmission wavelength band (1260-1650 nm), the optical cable satisfies the requirements of low bending loss, even for a bending radius (3 mm) smaller than that indicated in common current international standards. At the same time, the optical cable exhibits bending loss sensitivity at at least one wavelength outside the transmission wavelength band and in particular at at least one wavelength (in the described example at a plurality of wavelengths) below the measured cut-off wavelength of the cable.

Without wishing to be bound by any theory, generally speaking, in cabled configuration, bend sensitivity of the fundamental optical mode propagating along an optical fibre does not significantly change when the fibre is twisted in a cabled configuration. However, higher-order modes can propagate along the optical fibre and their power fraction may depend on the twisting of the fibre in the cable. The presence of higher order modes may then affect the total optical power of the light propagating along the fibre in the cabled configuration. The Applicant has noted that, generally speaking, given a wavelength band of single-mode transmission of an optical fibre, higher-order modes, when the fibre is properly designed, can account for a significant fraction of the transmission loss at wavelengths lower than the wavelengths of the single-mode window. Bend sensitivity at lower wavelengths can be often originated for a significant portion from higher order propagating modes.

Figure 5:
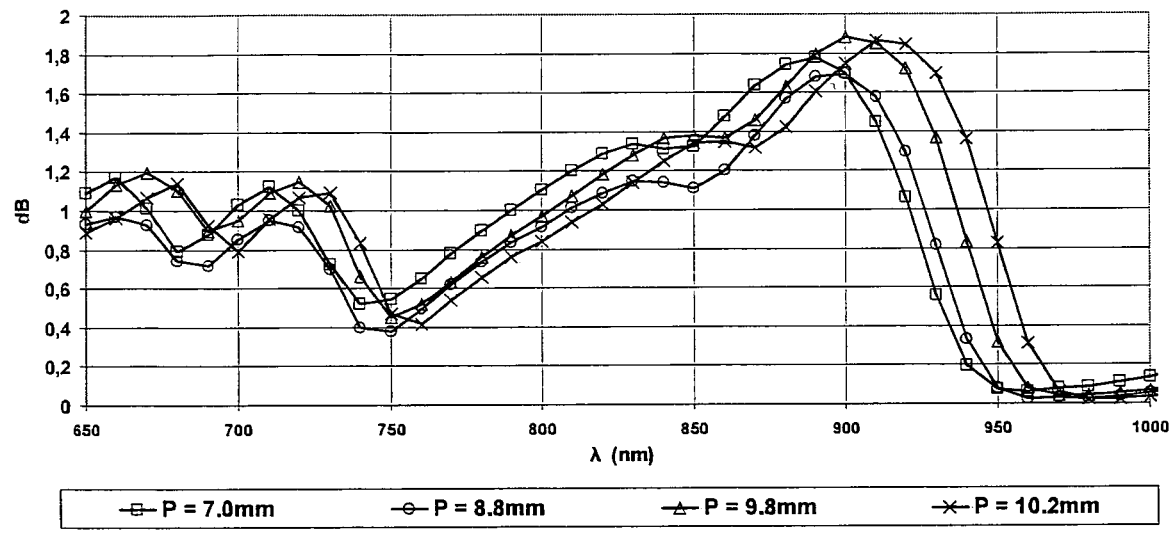
FIG. 5 is a graph showing experimental measurements of macrobending loss of an optical cable according to an embodiment of the present invention, measured in the wavelength band from 650 nm to 1000 nm for a cable length of 8.5 m and different values of twisting pitch.

FIG. 5 is a plot showing experimental measurements of attenuation of an optical cable according to another embodiment of the present invention, measured in the wavelength window from 650 nm to 1000 nm for different values of twisting pitch, P. Namely, the values of twisting pitches were: 7 mm (empty squares), 8.8 mm (empty circles), 9.8 mm (empty triangles), and 10.2 mm (crosses). Measurements were performed on cables having cable length, $L_{TOT}$, of 8.5 m, which were wound for one turn around a mandrel of bending radius of 5 mm. Results are relative to optical cables having a cable configuration of the type shown in FIG. 3 and comprising an optical fibre having, a refractive index profile of the example shown in FIG. 1. In the cabled configuration, the optical fibre was twisted around an aramid yarn DTEX 2 threads (i.e. the central element). The cut-off wavelength of the cables measured after propagation over the cable length of 8.5 m for a twisting pitch of 7 mm is of about 1260 nm.

It can be observed that, within the range of twisting pitches considered in the experiments reported in FIG. 5 (7-10 mm), a variation of twisting pitch does not significantly affect the sensitivity to bending in the wavelength region considered. In particular, for wavelengths between 650 nm and 900 nm bending loss is not smaller than about 0.4 dB. The measured attenuation induced by the 5 mm loop on the fibre used in all the samples at wavelengths of 1550 nm, 1625 nm, 1650 nm is less than 0.1 dB.

In some preferred embodiments, the twisting pitch and the twisted length of the at least one optical fibre comprised in the cable are selected so as to obtain single-mode transmission after propagation over the cable for wavelengths equal to or larger than 1260 nm.

Figure 6:
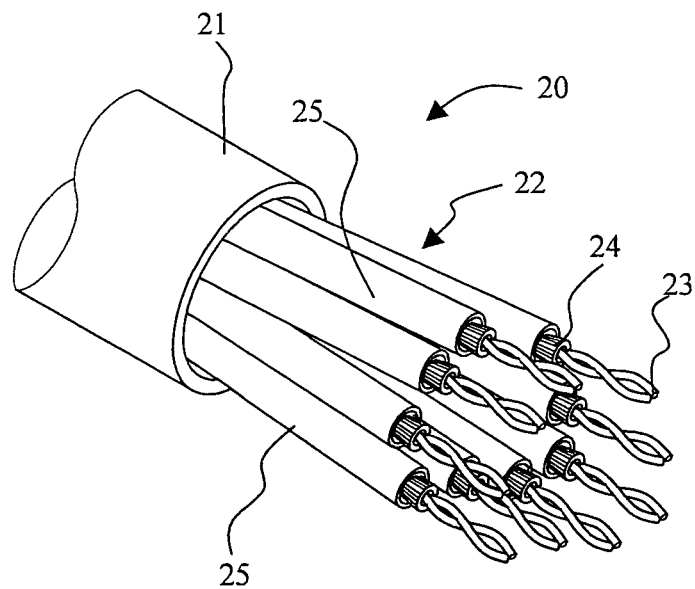
FIG. 6 is a schematic perspective view of a distribution optical cable according to an embodiment of the present invention.

FIG. 6 is a schematic perspective view of a distribution optical cable according to an embodiment of the present invention. The distribution cable 20, which can be used for instance for intra-building, risers, and plenum applications, comprises a bundle 22 of drop cables 25, wherein at least one optical cable of the bundle, and preferably each of the plurality of drop cables, has cable length and a measured cut-off wavelength after propagation over the cable length and comprises at least one twisted optical fibre 23 having an attenuation not smaller than a first threshold value at a predetermined test wavelength smaller than the measured cut-off wavelength when wound for one turn at a bending radius not larger than 5 mm and an attenuation below a second threshold value as measured at an operative wavelength equal to or larger than the measured cut-off wavelength when wound for one turn at a bending radius equal to at least a minimum bending radius. Each drop cable can be split from the distribution cable and then branched directly to individual subscribers. Accordingly, an access distribution network presenting low bending losses- and single-mode transmission from the MDU or the central office down to the user's terminals can be obtained.

In the embodiment illustrated in FIG. 6, the drop cables of bundle 22 are of the type illustrated in FIG. 2 and comprise a twisted pair of optical fibres 23, optionally surrounded by strengthening members 24. The bundle 22 of drop cables is enclosed by a tubular outer sheath 21, made for instance by a flame-retardant thermoplastic material, such as an LSOH material. Although not shown in FIG. 6, at least one reinforcing element can be embedded into the sheath and disposed along the length of the cable, so as to reduce mechanical stresses on the optical fibres due to tensile forces. Usually the reinforcing element can be made from a glass reinforced polymer (GRP) rod or can be an aramid rod.

Figure 7:
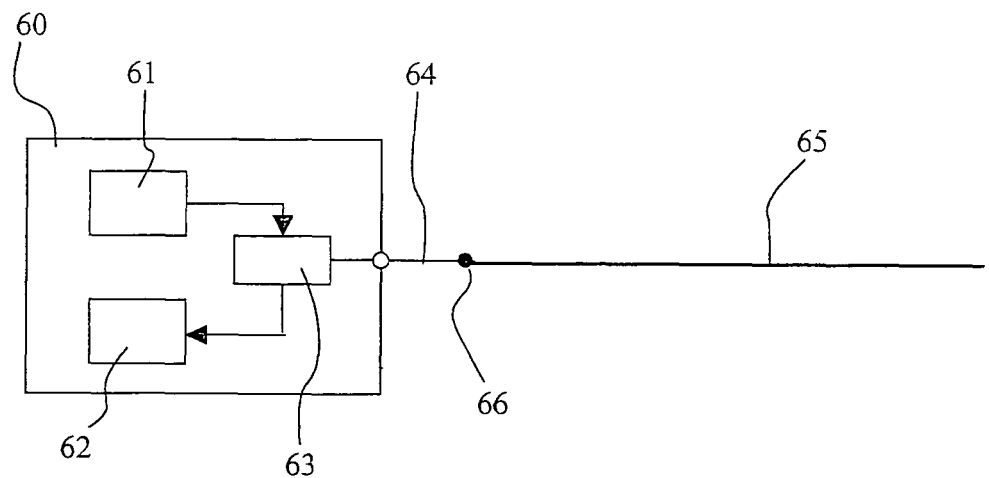
FIG. 7 is a block diagram for illustrating the operating principles of an OTDR measurement technique in an optical cable, according to an embodiment of the invention.

FIG. 7 is a schematic diagram for illustrating the operating principles of an OTDR measurement technique in an optical cable according to an embodiment of the invention. An optical time domain reflectometer as sampling apparatus 60 is used to inject probe optical signals in an optical cable 65 to be monitored and to analyse the backscattered and/or reflected optical signal, referred in general to as the returned signal, received from the cable. The optical cable 65 has a cable length and comprises at least one optical fibre extending along the cable longitudinal direction The at least one optical fibre of the cable exhibits an attenuation not smaller than a detection threshold value at at least one test wavelength that is below wavelengths of the transmission wavelength band of the optical cable. Preferably, the at least one optical fibre is helically twisted around a longitudinal axis with a twisting pitch for a twisted length extending along at least a portion of the cable length. For example, cable 65 has a configuration shown in FIG. 2 or in FIG. 3.

The sampling apparatus 60 comprises at least one optical source 61 capable of generating a probe optical signal at a probe wavelength that corresponds to the test wavelength of the optical fibre comprised in the cable to be measured. The optical signal generated by the optical source 61 is introduced in an optical coupler 63 that directs it into an optical fibre pigtail 64 connected, by means of a connection point 66, to an input end of the optical fibre of cable 65. Typically, optical signals for testing are pulsed signals centred at a predetermined wavelength, which is selected to correspond to the test wavelength where the optical fibre exhibits bend sensitivity, and with a given pulse width that can be generally tuned in accordance to some setting parameters in a manner per se known. The probe optical pulse propagates along the optical fibre and is backscattered and/or (Fresnel) reflected by loss-originating centres along the optical path of the probe signal, such as splices, connection points and micro- and macro-bending losses. As is well known, the OTDR technique is a distributed sensing technique that permits the localisation of the perturbations. In some OTDR measuring methods, the time delay between the signal detected from the fibre end or from any perturbation across the fibre and the probe optical pulse is measured and this measurement allows to derive the information about a localised perturbation, provided that the index of refraction in the fibre core or the group velocity of light propagation is known. Measurement of the returned power as a function of time or position in the fibre gives the information about the local distribution of the attenuation coefficient along the fibre. The returned optical signal travels in a reverse direction to the probe optical pulse and is directed back to the sampling apparatus 60, for example enters the optical coupler 63, which is connected to an optical receiver 62 which receives the returned light.

It is to be understood that the sampling apparatus can comprise a first and a second output for respectively launching and receiving optical signals.

Although not indicated in the figure, the sampling apparatus can comprise conventional optical and/or electrical devices and electro-optical converters together with electronic circuitry and processing units. The returned signal detected by the optical receiver is processed in a manner known per se and the transmission loss distribution along the fibre (cable) length can be derived.

In an exemplary embodiment, the optical cable to be monitored comprises an optical fibre having an attenuation not smaller than a detection threshold value at a test wavelength of 850 nm and the optical source of the OTDR sampling apparatus is a laser diode, such as a VSCEL diode, emitting optical pulses at a central wavelength of 850 nm.

In some embodiments, the sampling apparatus is provided with an optical source of variable wavelength, i.e. capable of generating optical signals at different wavelengths, or with a plurality of optical sources, each source being capable of generating an optical signal at a test wavelength. In this way, it is possible to monitor optical cables comprising optical fibres having predetermined but different test wavelengths at which the fibres are bend sensitive.

Measurements, are preferably carried out after laying down the optical cable to be measured so as to detect the presence of harmful bends in the deployed cable.

According to an aspect of the present invention a method for detecting faulty laying down of an optical cable is provided, the cable exhibiting a measured cut-off wavelength measured after propagation over a cable length. The method comprises providing an optical cable for transmitting optical signals including at least one optical fibre having an attenuation not smaller than a first threshold value at a predetermined test wavelength smaller than the measured cut-off wavelength and an attenuation below a second threshold value as measured at an operative wavelength equal to or larger than the measured cut-off wavelength; laying the optical cable, and measuring the attenuation in the at least one optical fibre at the predetermined test wavelength. According to some preferred embodiments, measuring the transmission loss in the optical cable uses an optical time domain reflectometer and comprises: optically connecting the optical time domain reflectometer to an input end of the at least one optical fibre; launching a probe optical signal at the test wavelength into the input end and measuring, after the launching of the test optical signal, the returned signal from the optical fibre. From the returned signal, the attenuation of the fibre in cabled configuration after propagation over the cable length is determined.

Preferably, the method comprises providing an optical cable for transmitting optical signals including at least one optical fibre having a match-clad type profile comprising a core region surrounded by a cladding region, the core region having an outer core radius and a maximum relative refractive index percent. Preferably, providing an optical cable comprises selecting the test wavelength by selecting a value of maximum relative refractive index percent in the range of 0.5% to 1% and selecting a value of outer core radius in the range of 4 µm to 7 µm.

The following section relates to the effect the twisting of the optical fibre may have in the cut-off wavelength of the cable comprising the fibre.

Twisting the optical fibres around each other imparts a curvature to both fibres, which is characterized by a radius of curvature, ρ, given by the following relation $$\rho = \frac{P^2}{(2\pi)^2 R} + R \quad (2)$$

where P is the twisting pitch and R is the fibre radius. The twisting pitch P is the distance along the helical axis (i.e., Z axis in FIG. 2) to get a full rotation of the optical fibre.

The length of the optical fibre within each single pitch, $L_p$, is given by $$L_p = \sqrt{P^2 + (2\pi R)^2} = 2\pi\sqrt{\rho R} \quad (3)$$

Figure 8:
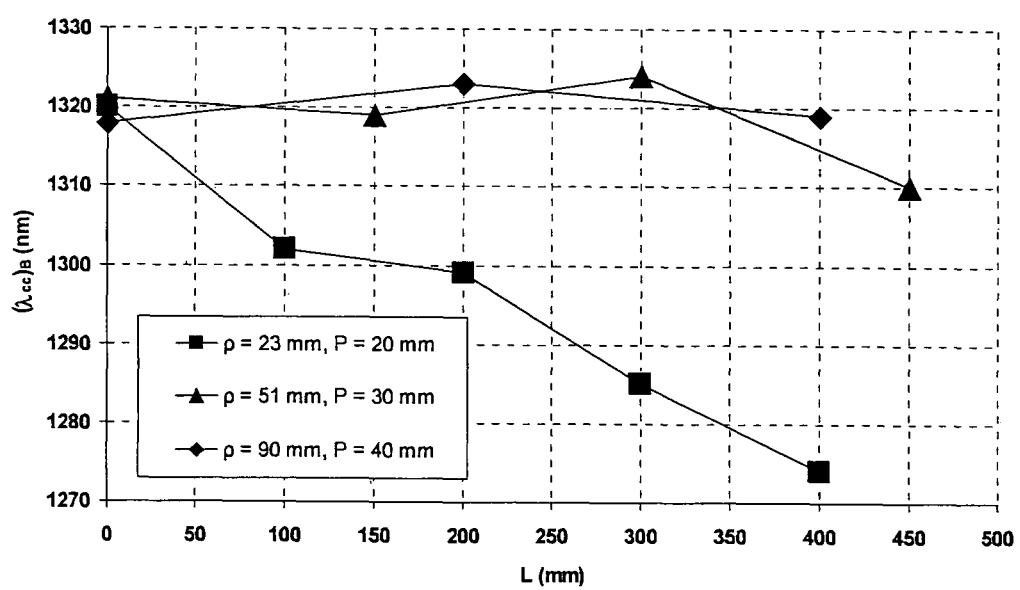
FIG. 8 is plot showing experimental measurements of the cable cut-off wavelength of an optical cable, $(\lambda_{cc})_B$, comprising two tight-buffered optical fibres of outside diameter of 900 μm twisted around each other, as a function of the twisted length, L (in mm).

FIG. 8 reports experimental measurements of the cable cut-off wavelength of the optical cable, $(\lambda_{cc})_B$, for an optical cable of the type shown in FIG. 2, which is measured by taking a 22 m-long span length of optical cable ($L_{TOT}$=22 m), whose central 20 m portion is left substantially uncoiled, by extracting the two 1 m-long terminal portions of cable, and by inserting a 40 mm-diameter loop for each terminal portion (experimental conditions corresponding to those prescribed in the IEC-60793-1-44 standards, method B). The plot of FIG. 8 shows, in ordinate, the cable cut-off wavelength (in nm) of the cable $(\lambda_{cc})_B$, and the length of the optical cable along which the optical fibres are twisted, referred to as the twisted length, L, (in mm) in abscissa. The cable comprises two buffered optical fibres of outside diameter of 900 µm (R=0.45 mm) twisted together. Each optical fibre has a cable cut-off wavelength, $(\lambda_{cc})_A$, of about 1320 nm and MFD of 8.6 µm. The cable cut-off wavelength of the optical cable is plotted as a function of the twisted length, L, for three different twisting pitches, of 20 mm (squares), 30 mm (triangles) and 40 mm (diamonds), corresponding to radii of curvature, ρ, of 23 mm, 51 mm and 90 mm, respectively. It is to be understood that $L=N\times L_p$, where N is the number of pitches and $L_p$ is given by Eq. (3). The twisted length, L, is smaller than the length portion of the fibre(s) utilized in the twisting by a factor equal to $\sqrt{1-R/\rho}$.

Experimental results of FIG. 8 show a pronounced decrease of the values of $(\lambda_{cc})_B$ with increase of the twisted length, L, especially for ρ=23 mm, which corresponds to a twisting pitch P=20 mm. For ρ=51 mm (P=30 mm), a significant decrease of $(\lambda_{cc})_B$ is observed for L=450 mm.

Results show that twisting a sufficiently long fibre portion with a sufficiently short twisting pitch (or sufficiently small radius of curvature), so as to reduce the cable cut-off wavelength of the optical cable, can produce an optical cable having a low macrobending loss and suitable for single-mode transmission at wavelengths above the value of cable cut-off wavelength required by the common optical transmission standards.

It is noted that the values of $(\lambda_{cc})_A$ and $(\lambda_{cc})_B$ determined according to the foregoing definitions are expected to be substantially equal to each other, were the fibre(s) untwisted.

According to some preferred embodiments, the twisted pitch, P, is selected in the range from 5 to 30 mm, preferably from 5 to 20 mm, wherein a suitable value will be selected within that range by taking into account the values of $(\lambda_{cc})_A$, and preferably of MFD, of the at least one optical fibre comprised in the cable.

According to some preferred embodiments of the invention, the twisted length and the twisting pitch are selected such that the optical cable exhibits a measured cut-off wavelength (namely, measured after propagation over the length of the optical cable) equal to or lower than 1260 nm. In this way, for a cable having a total length $L_{TOT}$, which extends from an input end apt to receive optical signals to an output end, single-mode optical signals emerge at the output end of the optical cable.

For a given twisting pitch, the twisted length L of the optical cable should be sufficiently long to cause the higher-order modes to fade away at wavelengths not smaller than a desired cut-off wavelength and to obtain an optical cable of total length $L_{TOT}$ of single-mode transmission. Preferably, the twisted length, L, approximately corresponds to the whole cable length, $L_{TOT}$. This may ease installation of the optical cable, especially if the cable needs to be cut or shortened to match it with the connectors or to fit it into an installation pathway. In that case, the installer would not need to know where the twisted portion is positioned along the cable length. Furthermore, this embodiment may guarantee that the optical cable is actually single-mode for its whole length $L_{TOT}$ (when L is greater than $L_{min}$). It is to be understood that approximate equality between the twisted length of the fibres and the total length of the optical cable means that the fibres are twisted along most of the total length of the cable, with the exception of a few percent of the length, usually at the terminal portions of the cable, where the fibres can be untwisted for a distance necessary for connectorizing or splicing the fibres (e.g., 2-4 cm at each cable end).

It is to be understood that equations (2) and (3) hold also for the twisting of the optical fibre illustrated in FIG. 3.

According to another embodiment, the twisted length may extend only along a portion of the total length of the optical cable. Only to provide a non-limitative numerical example: an optical cable of $L_{TOT}$=10 m comprises at least one optical fibre, which is helically twisted along an initial portion of the cable with a twisting pitch of 25 mm and a twisted length, $L<L_{TOT}$, of from 2 to 5 m. The twisted length has an input twisted end receiving the optical signals end an output twisted end. In a preferred embodiment, either the input twisted end or the output twisted end may correspond to the cable input end or to the cable output end, respectively. However, both the input twisted end and the output twisted end may also be located in an intermediate position along the cable, according to specific cable design requirements. At the output of the twisted portion of the optical fibre, i.e., at the output twisted end, transmission is single-mode. Preferably, the twisted portion is provided so that the output twisted end approximately corresponds to the output end of the optical cable. Under these conditions, the measured cut-off wavelength of the optical cable, i.e., at the cable output end, results to be equal to or smaller than 1260 nm. It is noted that, while it is contemplated to leave non-twisted portions in the cable, e.g., when external disturbances can be excluded, it is preferred to apply twisting in a cable portion as long as possible with respect to the total cable length.

Figure 9:
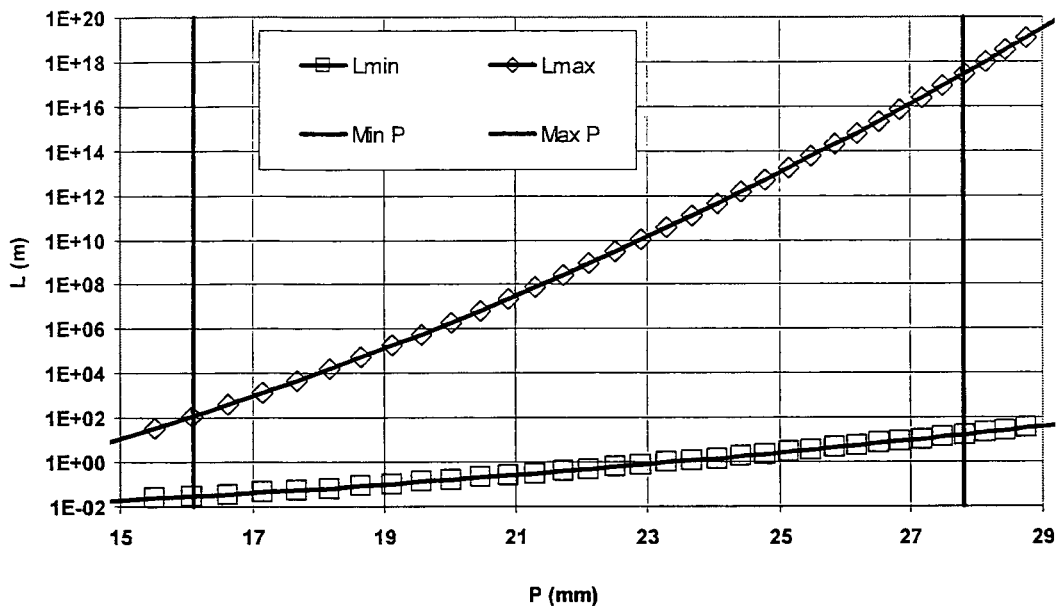
FIG. 9 is a plot of the twisted length, L, (in meters) as a function of twisted pitch, P (in mm) for an optical fibre having $(\lambda_{cc})_A$ of 1320 nm and MFD of 8.66 μm. Square and diamond symbols represent the minimum length ($L_{min}$) and the maximum length ($L_{max}$), respectively, of the twisted portion, which satisfy some conditions described hereafter with reference to the figure.

A variation of twisting pitch can affect the effective cut-off wavelength of the cable. FIG. 9 is a plot of the length, L, (in ordinate, meters) of the portion of the optical cable along which at least an optical fibre is twisted about an helical axis, i.e., the twisted length, as a function, in abscissa, of twisting pitch, P (in mm). The at least one optical fibre has $(\lambda_{cc})_A$=1320 nm and MFD=8.66 μm. Square and diamond symbols represent the minimum length ($L_{min}$) and the maximum length ($L_{max}$), respectively, of the twisted length, L, for a given twisting pitch for which the conditions described herebelow hold. The plot shows an approximately logarithmic-linear relationship between twisted length and twisting pitch (solid lines through data). By interpolating the data of FIG. 9, it is possible to infer an empirical mathematical relationship, and to determine the value of $L_{min}$ and $L_{max}$ for a given P.

In FIG. 9, the graphic area enclosed by the vertical thick solid lines and the lines through the values of $L_{min}$ and $L_{max}$ represent the range of values of P and L for which the following conditions are met:

(a) for a given twisting pitch, P, or equivalently for a given radius of curvature, the twisted length of the cable is long enough to make the higher-order modes (thus, $L_{P11}$) vanish, i.e., $(\lambda_{cc})_B$ is not more than 1260 nm, as measured according to the cabled configuration in IEC 60793-1-44 (2001-07), method B;

(b) the minimum cable length compatible with single-mode transmission is less than 20 m, where the length of 20 m corresponds to the uncoiled portion of the test length according to method B;

(c) the twisted length is such that the total attenuation of the fundamental mode ($L_{P01}$) along the optical cable caused by the twisting of the fibre(s) is less than 0.1 dB at a wavelength of 1550 nm, and (d) the value of P is such that the attenuation coefficient (i.e., attenuation per unit length) of the fundamental mode ($L_{P01}$) along the twisted length caused by the twisting of the fibre(s) is less than 1 dB/km at a wavelength of 1550 nm.

In general, condition (a) influences especially the value of $L_{min}(P)$, condition (b) the maximum value of P, condition (c) the value of $L_{max}(P)$, and condition (d) affects in particular the minimum value of P. For the example of FIG. 9, the range of P values meeting the above conditions is of from 17 mm to 28 mm, and is preferably selected of from 20 mm to 28 mm.

From results in FIG. 9 it can be observed that the upper limit of twisted length $L_{max}$ is not a concern in most access distribution network and PON applications, due to the fact that the total length of cables employed in access networks generally does not exceed a length of 1-2 km. For instance, for P=17 mm, $L_{max}$ is of 1.3 km, while for P=28 mm $L_{max}$ takes a very large value.

It is to be understood that conditions (a) to (d) are to a certain extent arbitrarily selected and they should not be construed as limitative of the present invention. More generally, conditions (a) to (d) only reflect typical desired properties in applications for single-mode signal transmission:

The values of L and P (or ρ) reported in FIG. 9 and in the following graphic (FIG. 10) and numerical examples' herein reported are customarily calculated by the skilled person in the art by using mathematical equations, per se known, for transmission of optical modes along an optical fibre and by taking into account the values of the cut-off wavelength, $(\lambda_{cc})_A$, and MFD of the twisted fibre or fibres. Within the teaching of the present invention, from the examples and ranges given herein, suitable values of P and L (or $L_{min}$ and $L_{max}$) can be readily determined by the skilled person for a given value of $(\lambda_{cc})_A$ selected in the range 1290-2200 nm and for a selected value of MFD, which is preferably comprised between 8.6 and 9.5 μm. More preferably, $(\lambda_{cc})_A$ is selected in the range from 1600 to 2000 nm.

Figure 10:
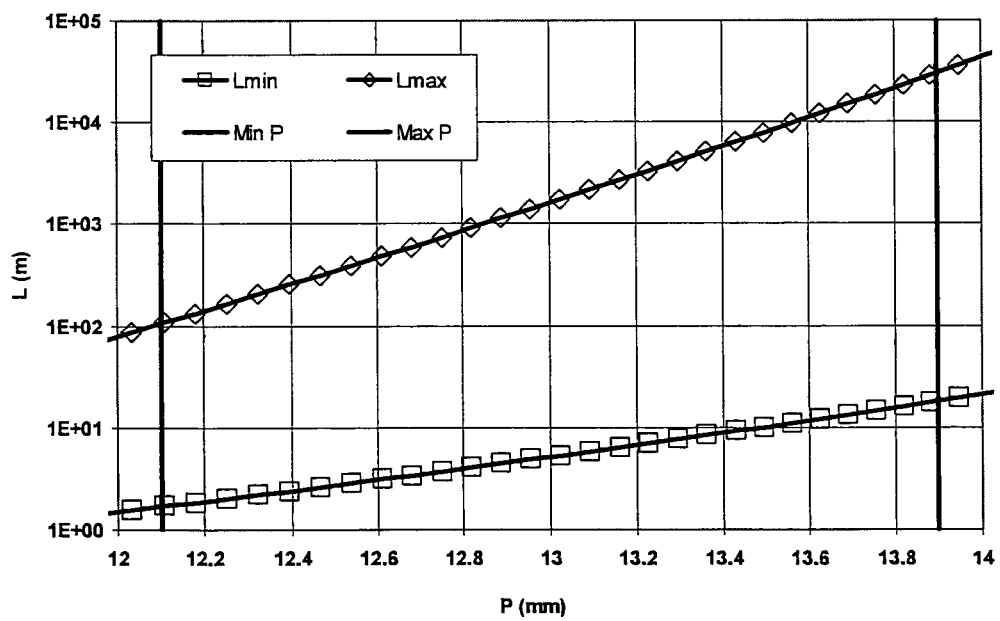
FIG. 10 is a plot of the twisted length, L, (in meters) as a function of twisted pitch, P (in mm) for an optical fibre having $(\lambda_{cc})_A$ of 1644 nm and MFD of 8.60 μm. Square and diamond symbols represent the minimum length ($L_{min}$) and the maximum length ($L_{max}$), respectively, of the twisted portion, which satisfy some conditions described hereafter with reference to the figure.

FIG. 10 is a plot of the twisted length, L, (in meters) as a function, in abscissa, of twisting pitch, P (in mm) of an optical cable comprising at least one optical fibre with $(\lambda_{cc})_A$=1644 nm and MFD=8.60 μm. Square and diamond symbols represent the minimum length ($L_{min}$) and the maximum length ($L_{max}$), respectively, of the twisted length, L, for a given twisting pitch. The graphic area delimited between the vertical thick solid lines and between lines through $L_{min}$ and $L_{max}$ data represents the range of values of P and L for which the above-described conditions (a) to (d) are met.

The range of P values of FIG. 10 meeting the above-described conditions (a) to (d) is of from 12 mm to 14 mm.

The foregoing is a description of various embodiments of the invention, but it is to be understood that other embodiments and examples may perform similar functions and/or achieve similar results. All such equivalent embodiments are within the scope of the present invention and intended to be covered by the appended claims.

In particular, although optical cables including at least one twisted optical fibre have been described with reference to an optical cable comprising one twisted optical fibre or a pair of twisted optical fibres, the present invention envisages an optical cable comprising more than two optical fibres twisted around each other, for instance three optical fibres twisted in a three-threaded plait.

The invention claimed is:

1. A method for detecting faulty laying down of an optical cable exhibiting a measured cut-off wavelength, measured after propagation over a cable length, comprising:

providing an optical cable for transmitting optical signals comprising at least one single-mode optical fiber having an attenuation equal to or larger than a first threshold value as measured when wound for one turn around a bending radius equal to or smaller than 5 mm at at least one predetermined test wavelength, the test wavelength being smaller than the measured cut-off wavelength and an attenuation smaller than a second threshold value as measured when wound for one turn around a bending radius equal to at least a minimum bending radius at an operative wavelength equal to or larger than the measured cut-off wavelength;

laying the optical cable; and measuring the attenuation in the at least one optical fiber at the predetermined test wavelength.

2. The method of claim 1, wherein the predetermined test wavelength is equal to or larger than 450 nm and smaller than 1260 nm.

3. The method of claim 1, wherein the at least one operative wavelength is in a transmission wavelength range of 1260 nm to 1675 nm.

4. The method of claim 1, comprising measuring the attenuation in the optical cable with an optical time domain reflectometer.

5. The method of claim 4, wherein measuring the attenuation in the optical cable comprises:

optically connecting the optical time domain reflectometer to an input end of the at least one optical fiber;

launching a probe optical signal at a probe wavelength corresponding to a test wavelength into the input end of the at least one optical fiber;

measuring, after the launching of the probe optical signal, a returned signal from the at least one optical fiber; and from the returned signal, determining the attenuation of the fiber in cabled configuration after propagation over the cable length.

6. The method of claim 1, wherein the at least one optical fiber has a cable cut-off wavelength larger than the measured cut-off wavelength and is helically twisted around a longitudinal axis with a twisting pitch for a twisted length extending along at least a portion of the cable length so that, when the at least one optical fiber is cabled, the cable cut-off wavelength of the optical cable is equal to the measured cut-off wavelength.

7. An optical cable for transmitting optical signals, the optical cable having a cable length and exhibiting a measured cut-off wavelength measured after propagation over the cable length, comprising:

at least one single-mode optical fiber having an attenuation equal to or larger than a first threshold value as measured when wound for one turn around a bending radius equal to or lower than 5 mm at at least one predetermined test wavelength smaller than the measured cut-off wavelength and an attenuation smaller than a second threshold value as measured when wound for one turn around a bending radius equal to at least a minimum bending radius at an operative wavelength equal to or larger than the measured cut-off wavelength.

8. The optical cable of claim 7, comprising:

the at least one single-mode optical fiber for testing use; and at least one bend insensitive single-mode optical fiber dedicated to transmission.

9. The optical cable of claim 7, wherein the at least one single-model optical fiber has a cable cut-off wavelength larger than the measured cut-off wavelength and is helically twisted around a longitudinal axis with a twisting pitch for a twisted length extending along at least a portion of the cable length so that, when the at least one optical fiber is cabled, the cable cut-off wavelength of the optical cable is equal to the measured cut-off wavelength.

10. The optical cable of claim 7, wherein the minimum bending radius is 7.5 mm.

11. The optical cable of claim 7, wherein the minimum bending radius is 5 mm.

12. The optical cable of claim 7, wherein the measured cut-off wavelength is equal to or smaller than 1260 nm.

13. The optical cable of claim 12, wherein the at least one predetermined test wavelength is equal to or larger than 450 nm and smaller than 1260 nm.

14. The optical cable of claim 7, wherein the cable cut-off wavelength of the at least one optical fiber is equal to or larger than 1290 nm.

15. The optical cable of claim 7, wherein the at least one optical fiber is a match-clad type and comprises a core region surrounded by a cladding region, the core region having an outer core radius and a maximum relative refractive index percent.

16. The optical cable of claim 15, wherein the outer core radius is 4 µm to 7 µm and the maximum relative refractive index percent is 0.5% to 1%.

17. The optical cable of claim 15, wherein the at least one optical fiber is a step-index single-mode optical fiber.

18. The optical cable of claim 9, wherein the twisting pitch is 5 to 30 nm.

\* \* \* \* \*